United States Patent [19]
Hasson et al.

[11] Patent Number: 5,338,317
[45] Date of Patent: Aug. 16, 1994

[54] ROTATIONAL SURGICAL INSTRUMENT HANDLE

[75] Inventors: Harrith M. Hasson, Chicago, Ill.; Edward D. Pingleton; Paul G. Thomson, both of Fillmore, both of Ind.

[73] Assignees: Vance Products Incorporated; Cook Urological Incorporated, Spencer, Ind.

[21] Appl. No.: 695,297

[22] Filed: May 3, 1991

[51] Int. Cl.$^5$ .............................................. A61B 17/28
[52] U.S. Cl. .................................... 606/206; 606/170; 606/174; 128/751
[58] Field of Search ............... 606/166, 167, 170, 174, 606/205–210; 128/750, 751, 752, 753, 754, 755; 30/137; 294/99.2, 115

[56] References Cited

U.S. PATENT DOCUMENTS

| | | | |
|---|---|---|---|
| 86,016 | 1/1869 | Howell | 606/127 |
| 273,243 | 3/1883 | Adams . | |
| 3,506,012 | 4/1970 | Brown . | |
| 3,995,619 | 12/1976 | Glatzer | 606/171 |
| 4,039,326 | 8/1977 | Soos . | |
| 4,085,743 | 4/1978 | Yoon | 606/206 |
| 4,174,715 | 11/1979 | Hasson | 606/206 |
| 4,467,802 | 8/1984 | Maslanka | 606/206 |
| 4,516,575 | 5/1985 | Gerhard et al. | 606/167 |
| 4,712,547 | 12/1987 | Bonnet | 606/170 |
| 4,760,848 | 8/1988 | Hasson . | |
| 4,865,030 | 9/1989 | Polyak | 606/127 |
| 4,994,079 | 2/1991 | Genese et al. | 606/206 |

FOREIGN PATENT DOCUMENTS 9001297 2/1990 World Int. Prop. O. .......... 606/167

*Primary Examiner*—Michael H. Thaler
*Assistant Examiner*—William Lewis
*Attorney, Agent, or Firm*—Richard J. Godlewski

[57] ABSTRACT

A rotational surgical instrument including a working head connected to a rotatable, pencil-like handle. The handle includes a casing with distal and proximal end caps, an elongated outer member extending into the casing, and a actuation link extending from the distal end cap through the casing and elongated member to the working head. An actuating mechanism is positioned distally from the distal end cap about the proximal portion of the elongated member for slidably actuating the working head between and open and closed positions. A compression spring is included in the passageway of the casing around the actuation link between the proximal end cap and the proximal end of the elongated member to return the working head to the nonactuated position. Keyed surfaces are included within the passageway of the casing and attached to the distal end of the casing and the proximal end of the elongated member for preventing rotation of the elongated member with respect to the casing and actuation link. A spring is also positioned between the distal end cap and the actuating mechanism for varying the combined tension of the two springs for operating the handle. The variable tension spring is varied by rotating a knob of the actuating mechanism which adjusts the distance from the distal end cap.

18 Claims, 4 Drawing Sheets

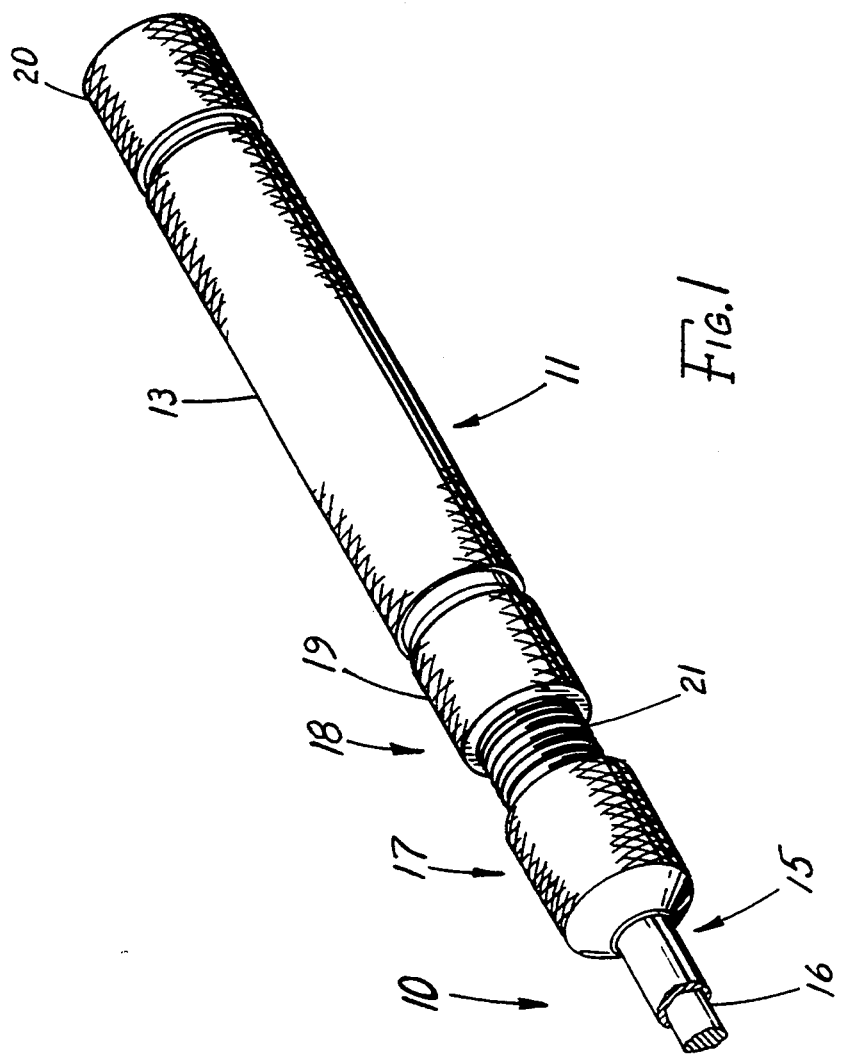
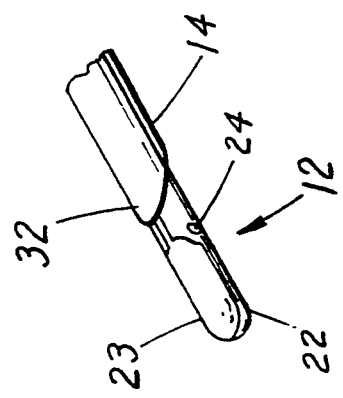
FIG. 1

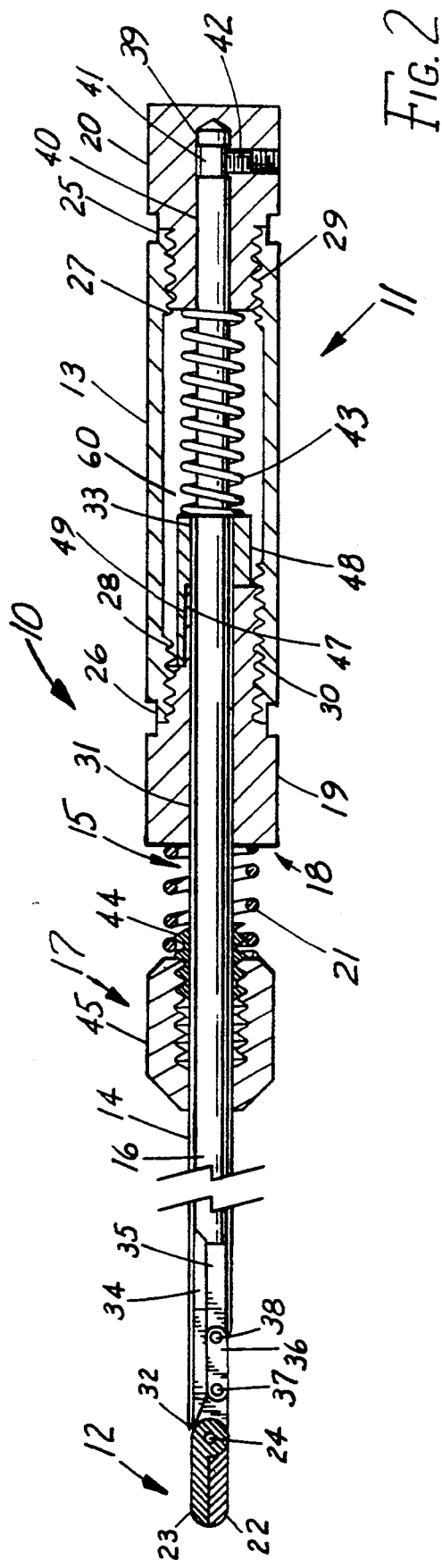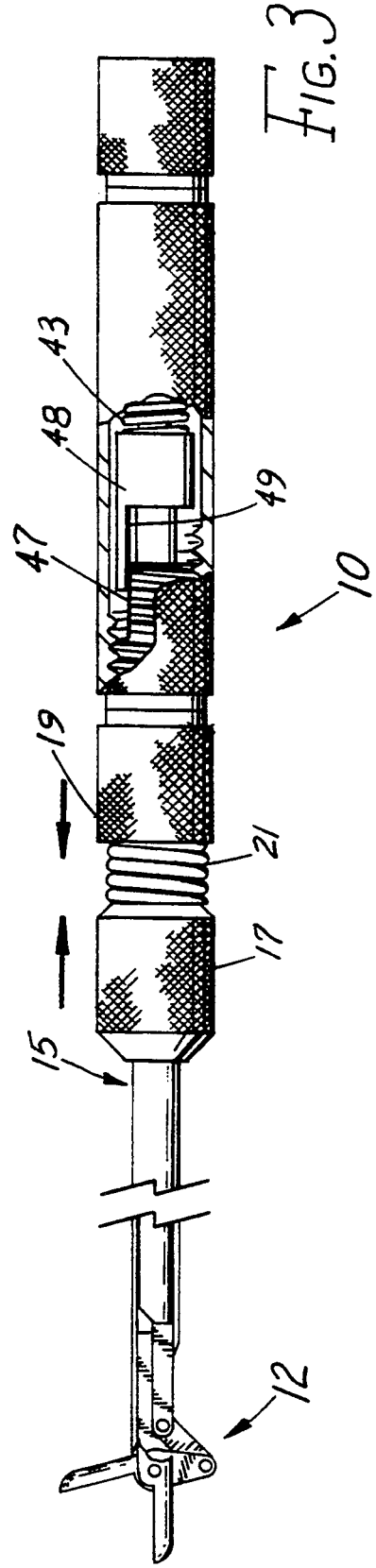

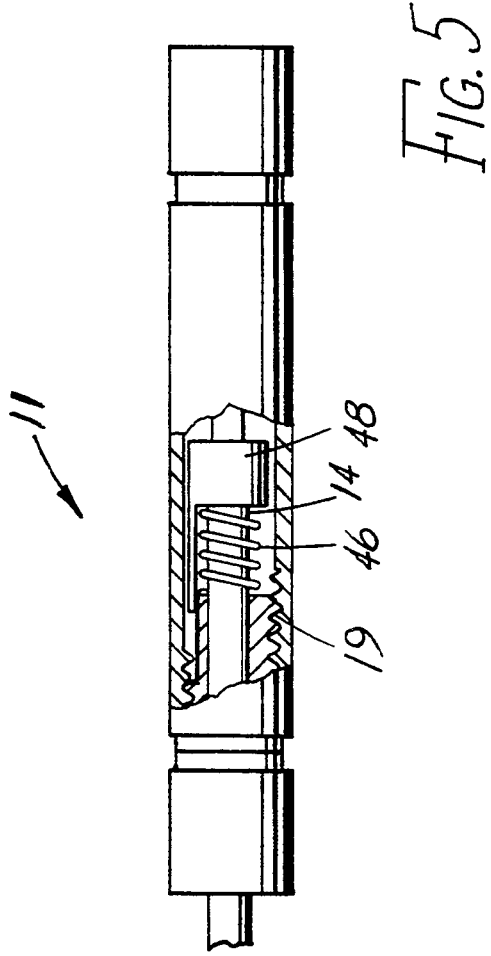

ROTATIONAL SURGICAL INSTRUMENT HANDLE

TECHNICAL FIELD

This invention relates to surgical instruments and, in particular, a rotational surgical instrument handle having a working head connected to a slidable link that is controllable from a location remote from the working head.

BACKGROUND OF THE INVENTION

Muscles that control motion of the fingers are physiologically capable of more precise motion than muscles that control the wrist or forearm. Devices that are designed for manipulation by the fingers allow physicians to use optimum dexterity and control during delicate surgical procedures such as microsurgery and laparoscopy. These procedures require the use of devices with jaws or blades that are precisely controllable for preventing damage to tissue adjacent the treated site. Furthermore, the devices should be convenient to use for minimizing operative time and muscle fatigue of the physician. To date, surgical devices that are readily and precisely controlled by the muscles of the fingers are very limited.

One prior art device has a scissors-type grip for actuating a sliding cable or link within a flexible casing to open or close cooperating jaws or blades. A problem with this device is that the rotation thereof requires turning the grip using muscles of the wrist. Another problem with this device is that the device is not rotatable about the axis of the device casing unless the casing is maintained perfectly straight. These problems limit the physician's degree of control over the device. Yet another problem with this device is that the working head is not fixedly positioned with respect to the axis of the device. The working head may nutate when the device is rotated, thereby damaging tissue adjacent the treatment site. Still another problem with the device is that maintaining closure of the jaws or blades requires constant pressure on the grip, which is awkward and inconvenient for a physician during a procedure. In addition, applying constant pressure to the grip causes muscle fatigue and further loss of control over the device.

Another nonsurgical device as disclosed in U.S. Pat. No. 273,243 of Adams is a pair of pivotally interconnected tongs that are spring-biased closed for grasping and holding an object. The tongs are actuated open by depressing a control rod on the proximal end of a handle for compressing the spring. A problem with this device is that the actuation portion of the working head is not designed for use in delicate medical procedures. For example, the actuation portion includes interconnecting links that extend between several pivot pin connections. The links project laterally at abrupt angles when the tongs are actuated. These lateral projections may damage tissue adjacent the treated site. In addition, the working head is easily nutated when the device is rotated or positioned at an acute angle with respect to the object to be grasped. Furthermore, grasping of the object and subsequent manipulation requires repositioning of the hand about the proximal end of the device. As a result, the instrument can not be controlled with the finesse and delicacy required for surgical procedures.

Another device as disclosed in U.S. Pat. No. 3,506,012 of Brown is a surgical instrument for removing a polyp by connecting and disconnecting a distal clamp unit. The device includes a longitudinally actuated control rod, which also rotates for opening and closing a pair of distal pivoted jaws. A problem with this device is that actuating the jaws requires two-hand manipulation. The tubular device body is firmly gripped by one hand so that a hand knob on the control rod is rotated to open or close the distal jaws. The control rod is pulled rearwardly for releasing the clamp unit. The use of two hands to manipulate the device is inconvenient for a physician and may lengthen the operative time of some procedures. Furthermore, using the muscles of the wrist and forearm diminishes the precision and control a physician has over the device, and adjacent tissue may be inadvertently damaged.

Another nonsurgical device as disclosed in U.S. Pat. No. 4,039,216 of Soos is a gun-grip grasping device with a manually operated lever that is pulled toward a fixed handle for closing two distal jaws and retrieving articles from the ground without bending over to pick them up. A problem with this device is that the device is actuated using the muscles of a closing hand rather than one or two fingers. Another problem with the device is that the jaws remain open when nonactuated. Furthermore, the operator has to maintain pressure on the lever to hold the jaws closed, which causes muscle fatigue.

Another prior art surgical device as disclosed in U.S. Pat. No. 4,760,848 of Hasson includes a working head with pivotally interconnected jaws and an actuating link for moving the element by pressing laterally with the thumb and finger of one hand on the control elements of a casing. Although suited for its intended purpose, this device during repeated actuation quickly fatigues the muscles of the physician's fingers. Furthermore, control of the device is compromised during actuation and even more so during repeated actuations.

SUMMARY OF THE INVENTION

The foregoing problems are solved and a technical advance is achieved by an illustrative rotational surgical instrument handle that is connectable to a working head having at least two working positions. The instrument handle advantageously includes a cylindrical casing that is easily rotated and manipulated in the physician's hands by simple manipulation of the fingers. An actuating mechanism is easily grasped by two fingers of the physician's hand and is positioned distally from the distal end of the casing for actuating the working head with a simple pulling or pushing movement. The casing and actuating mechanism are easily rotated and manipulated by the physician without compromising control and positioning of the working head during delicate microsurgical procedures. The handle also includes an elongated member that extends from the working head and into the casing with the actuating mechanism positioned about a proximal portion thereof. An actuating link positioned and slidable within the passageway of the elongated member is connected to the working head for urging the working head between at least two positions when the actuating mechanism is operated.

The handle further advantageously includes a compression member positioned within the passageway of the casing about the proximal end of the actuation link and between the proximal ends of the casing and elongated member for maintaining and returning the working head to a given position when not actuated by the physician. This significantly reduces fatigue or the need for control of the instrument during nonactuated manipulation. Alternatively, an expansion member such as a spring may be positioned about the proximal end of the link between the distal end of the casing and the proximal end of the elongated member for returning and maintaining the working head in the other position.

To advantageously tailor or adjust the force for actuating the instrument to meet the varying strengths and comforts of individual physicians, another compression member is positioned between the actuating mechanism and the distal end of the casing about the elongated member. The actuating mechanism is slidable between first and second positions for actuating the working head. The actuating mechanism includes a finger-grasping cap that is rotatable to adjust the distance between the slidable actuating mechanism and the distal end of the casing. Varying this distance advantageously adjusts the actuation force necessary to compress the spring members and meet the comforts of the individual physician. This compression member is easily adapted to vary the actuating force necessary to urge the working head to either of the at least two working positions.

Many working heads require a link that is nonrotatable to maintain a fixed relationship between moving parts of the head when actuated such as with opening and closing tissue grasping jaws. Otherwise, rotation of the actuating link will bind the moving parts of the working head causing increased actuating force or preventing actuation of the working head. Advantageously, the rotational surgical handle includes a first keyed surface fixedly positioned about the distal end of the casing and a second keyed surface fixedly positioned about the proximal end of the elongated member and longitudinally engageable with the first keyed surface to prevent rotation of the link with respect to the elongated member.

To provide ready disassembly and cleaning of the instrument handle, the casing includes a removable distal end cap that has a longitudinal passageway for extending the elongated member and the link therethrough. The casing also includes a removable proximal end cap fixedly connectable longitudinally to the proximal end of the link.

The rotational surgical instrument handle is advantageously combined with the working head to provide a rotational surgical instrument that is easily and readily operable without undesired motion of the working head.

BRIEF DESCRIPTION OF THE DRAWING

FIG. 1 depicts an illustrative embodiment of the rotational surgical instrument of the present invention;

FIG. 2 depicts a partially sectioned side view of the instrument of FIG. 1 in a closed position;

FIG. 3 depicts a partially sectioned side view of the instrument of FIG. 1 in an open position;

FIG. 5 depicts a partially sectioned view of an alternative embodiment of the instrument of the present invention.

DETAILED DESCRIPTION

Figure 4:
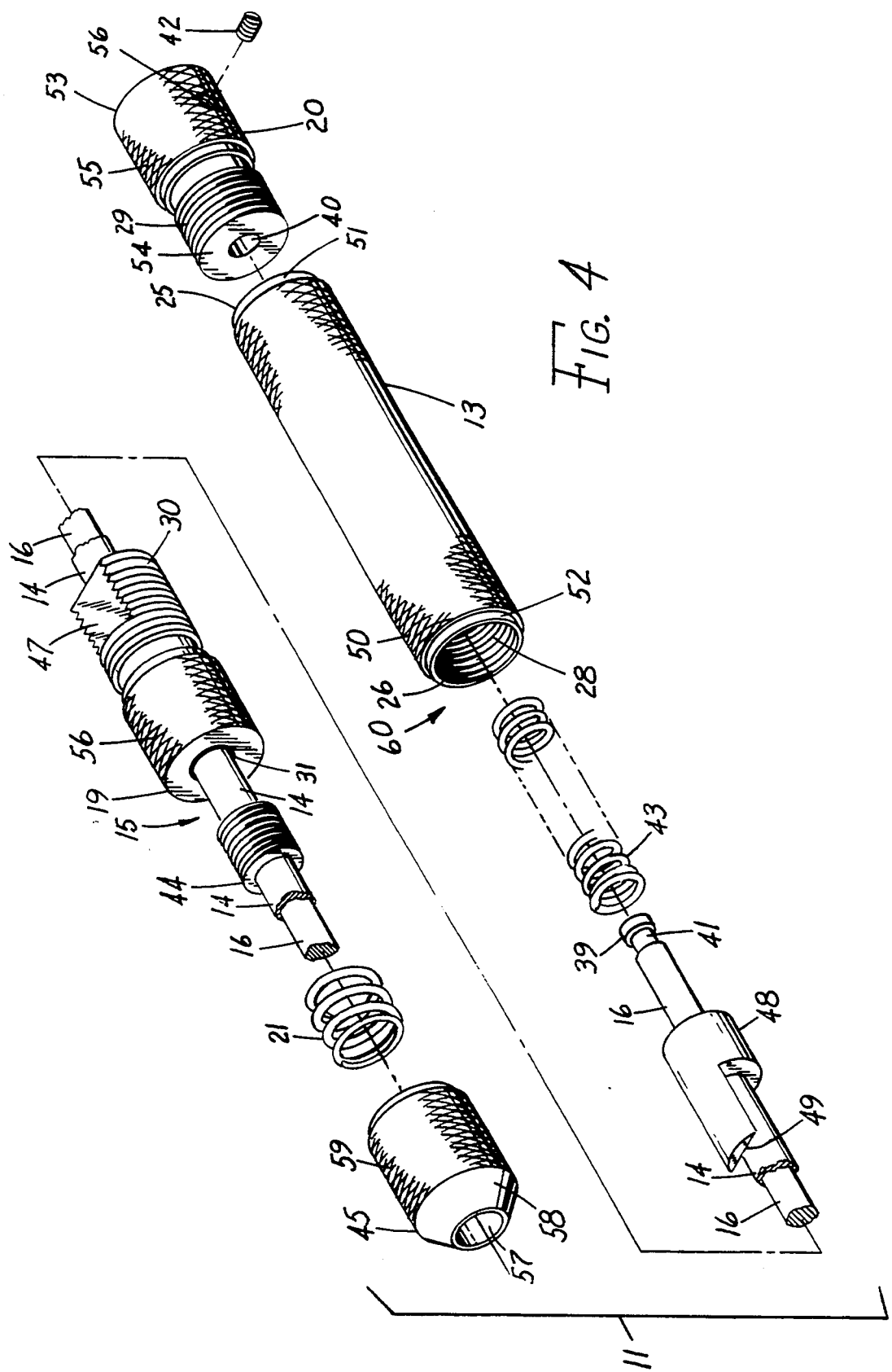
FIG. 4 depicts an exploded view of the instrument handle of FIG. 1.

Depicted in FIG. 1 is rotational surgical instrument 10 including nonactuated handle 11 and working head 12 in a closed position. The instrument handle includes cylindrical casing 13, elongated member 14 with proximal portion 15 extending into the hollow passageway of the casing, and actuation link 16 positioned and slidable within the passageway of the elongated member. The actuation link and elongated member are connected to the working head for urging the working head between open and closed positions. The instrument handle further includes an actuating mechanism 17 positioned distally from distal end 18 of the casing and connected around proximal portion 15 of the elongated member for actuating the working head between the open and closed positions. The casing includes removable distal end cap 19 and removable proximal end cap 20. The handle further includes a compression spring 21 positioned around proximal portion 15 of the elongated member between actuating mechanism 17 and distal end cap 19 for varying the force needed to operate the actuating mechanism and instrument. Working head 12 includes stationary jaw 22 and opposing movable jaw 23 interconnected by pivot pin 24. The stationary jaw extends from tapered distal end 32 of the longitudinal passageway of elongated member 15 and is connected thereto using, for example, silver solder. Movable jaw 23 operates between open and closed positions and is connected to the distal end of the actuation link by an interconnecting link and pins that will be described hereinafter.

Depicted in FIG. 2 is a partially cross-sectioned side view of surgical instrument 10 of FIG. 1 with working head 12 in the closed position. As shown, cylindrical casing 13 includes annularly recessed proximal and distal ends 25 and 26 and hollow longitudinal passageway 60 extending therebetween. The distal and proximal ends of the casing passageway include respective internal threads 27 and 28 for mating with external threads 29 and 30 of distal end cap 19 and proximal end cap 20, respectively. The mating threads of the end caps and longitudinal passageway permit ready disassembly, cleaning, and reassembly of the handle.

Proximal portion 15 of elongated member 14 comprising, for example, a stainless steel tube, slidably extends through distal end cap passageway 31 and into casing passageway 60. Elongated member tube 14 includes tapered distal end 32 fixedly connected to stationary jaw 22 of working head 12. Proximal end 33 of elongated member tube 14 is positioned in passageway 60 of the casing. Hollow passageway 34 extends longitudinally between the distal and proximal ends 32 and 33. Actuation link 16 comprising, for example, a stainless steel rod, extends through hollow passageway 34 of the elongated member and is slidable therein. Actuation link 16 includes distal end 35 connected to movable jaw 23 via interconnecting link 36 and pivot pins 37 and 38 positioned at the respective ends of the interconnecting link. Longitudinal movement of the actuation link within the passageway of the elongated member urges the movable jaw of working head 12 between the closed and open positions. The actuation link also includes proximal end 39 extending from the proximal end of the elongated member passageway, through casing passageway 60, and into hollow longitudinal passageway 40 of proximal end cap 20. Proximal end 39 of the actuation link includes an annular recess 41 of which set screw 42 extends therein. The set screw extends laterally through the proximal end cap for release of the actuation link and removal of the end cap. When the instrument handle is reassembled, the proximal end cap is screwed into the casing over the slidable link. The set screw is then extended into the annular recess to fixedly position the actuation link longitudinally in the handle.

The annular recess allows the set screw to be placed anywhere along the circumference of the actuation link when the handle is completely assembled.

The handle also comprises a first compression member spring 43 positioned within hollow passageway of the casing around the proximal end of link 16 and between distal end cap 20 and proximal end 33 of the elongated member. This compression spring pushes against proximal end 33 of the elongated member to return the working head to the closed position. To actuate the working head to the open position, actuating mechanism 17 is pulled by the physician compressing the spring and sliding link 16 toward the distal end of the elongated member tube. As a result, movable jaw 23 is forced to the open position via interconnecting link 36. Actuating mechanism includes an externally threaded sleeve 44 fixedly positioned by, for example, soldering, on proximal portion 15 of the elongated member. Internally threaded knob 45 extends over the working head and elongated member to engage the threads of the sleeve. A second compression spring member 21 is positioned between the proximal end of the threaded knob and the distal end of removable distal end cap 19. The actuating mechanism is slidable between actuated and nonactuated longitudinal positions from the distal end of the casing and, in particular, predetermined distances from the distal end cap. The distance between the actuating knob and the distal end of the end cap is varied by rotating the knob on the threaded sleeve. The compression force of spring member 21 is varied as a result of the distance between the knob and the end cap. This allows the physician to vary the tension or compression force necessary to pull the actuation mechanism longitudinally and urge the working head between the open and closed positions.

The proximal end of distal end cap 19 includes a first keyed surface 47 which includes a flattened surface extending longitudinally on the threaded end of the distal end cap. Proximal end 33 of the elongated member includes collar 48 fixedly positioned thereto and has a second keyed surface 49 extending longitudinally from the distal end thereof. Keyed surfaces 47 and 49 longitudinally engage each other to prevent rotation of the elongated member with respect to casing 13 and actuation link 16.

Depicted in FIG. 3 is a partially sectioned side view of rotational instrument 10 with working head 12 in the open position. Actuating mechanism 17 has been pulled toward the distal end of distal end cap 19 thereby compressing spring members 43 and 21. This is accomplished by the physician grasping the actuating mechanism by two fingers and pulling the actuating mechanism toward the casing with the casing fixed in the palm of the physician's hand. Alternatively, the palm can push against the casing to force the distal end of the distal end cap toward the actuating mechanism. Yet another way to actuate the handle is to grasp the actuating mechanism between the middle, index, and thumb with the casing lying in the crease between the index and thumb like one would normally hold a pencil. In such position, the instrument is easily rotated, turned, or manipulated as desired by the physician in performing delicate microsurgical procedures. When in the open position, the proximal end of the distal end cap 19 and collar 48 are separated with keyed surfaces 47 and 49 sliding longitudinally thereagainst. However, the keyed surfaces prevent the rotation of the elongated member with respect to the actuation link or handle casing. Alternatively, it is contemplated that these keyed surfaces may be eliminated such as to allow the physician to not only pull or push on the actuating mechanism but also rotate the elongated member to provide additional selection to a working head requiring such a rotational movement. As is also shown, the distance between the actuating mechanism and the distal end of the distal end cap can be varied to adjust the tension required to compress spring member 21.

Depicted in FIG. 4 is an exploded view of rotational surgical instrument handle 11 illustrating how the various components of the handle are formed and fit together. As shown, casing 13 comprises a titanium cylindrical tube approximately 2.210" in length and having an 0.500" outside diameter with a 0.049" wall thickness. The outside surface of the tube is knurled about the circumference thereof with a fine, diamond-shaped, male knurl 50 with a 30 degree spiral and 30 threads per inch increasing in diameter by approximately 0.015". Proximal end 25 and distal end 26 are annularly recessed to form respective smooth outer surfaces 51 and 52 approximately 0.06" in length with a 0.465" maximum outer diameter. Proximal and distal ends 25 and 26 of longitudinal passageway 60 include respective internal threads 27 (not shown) and 28 of 7/16"–20 threads. Each length of internal thread extends for approximately 0.8". Proximal end cap 20 comprises a 0.500" outside diameter titanium rod approximately 0.870" in length with proximal end 53, distal end 54, and 0.126" diameter longitudinal passageway 39 extending inwardly from distal end 54 for approximately 0.800" along the center line of the rod. External threads 29 are 7/16"–20 threads extending for a length of approximately 0.245". The circumference of the proximal end of the rod is knurled with knurl 55, which is a fine, diamond-shaped, male knurl as previously described. Laterally extending passageway 56 is drilled to longitudinal passageway 39 and tapped with 5–40 threads approximately 0.250" from proximal end 53 of the rod. Set screw 42 is screwed into laterally extending passageway 56 and into annular recess 41 of actuation link 16. Spring member 43 is approximately 1.25" in length with an outside diameter of approximately 0.187" for extending into passageway 60 of the casing and over actuation link 16. The elastic modulus of the spring is selected to provide compression as is suitable to the grasp of the physician's hand. The tension is also sufficient to force elongated member 14 into a fully outwardly extended position. Actuation link 16 comprises a 0.125" diameter 300 series stainless steel rod approximately 14.8" in length. The proximal end of the rod includes annular recess 41 whereas the distal end includes a forked slot at the distal end for receiving interconnecting link 36. Elongated member 14 comprises approximately a 14.125" length of 300 series stainless steel tubing having an outside diameter of approximately 0.180" and an inside diameter of approximately 0.165" for receiving actuation link 16 therein. Fixedly attached using, for example, silver solder, about the proximal end of the tube is collar 48 approximately 0.340" in length with an outside diameter of 0.375" and a 0.180" passageway extending therethrough. Keyed flat surface 49 extends from the distal end of the collar for approximately 0.410" to mate with the flattened keyed surface 47 of the distal end cap. Positioned about proximal portion 15 of the tube is externally threaded sleeve 44 with 5/16"–24 threads having an outside diameter of approximately 0.305" extending for a length of 0.300". The threaded sleeve is silver soldered, for example, about proximal portion 15 of the elongated member.

Distal end cap 19 is a 0.500" diameter titanium rod approximately 1.125" in length. Hollow longitudinal passageway 31 is 0.180" in diameter centered longitudinally through the rod. The circumference of the distal end of the rod is knurled with knurl 56, which is a fine, diamond-shaped, male knurl as previously described. The knurling extends for approximately 0.500 ∝ from the distal end of the end cap. The proximal end of the end cap includes 7/16"-20 threads 30 with flattened surface 47 extending for about 0.395". Alternatively for ease of manufacture, distal end cap 19 may be pressed into cylindrical casing 13 rather than be threaded.

Actuating knob 17 is 0.500" diameter titanium rod approximately 65" in length with a 0.180" longitudinal passageway 57 extending about the center line therethrough. The distal end of the knob includes a 50 degree taper 58 with knurling 59 extending for approximately 0.520". Knurling 59 is as was previously described. The proximal end of the knob is drilled and tapped with internal 5/16"-24 threads for approximately 0.400". These threads mate with the external threads of the threaded sleeve for adjusting the tension applied to spring member 21 which slides over the threaded sleeve between the distal end of end cap 19 and the proximal end of the actuating knob.

Depicted in FIG. 5 is a partially sectioned view of an alternative embodiment of instrument handle 11 with spring member 41 positioned around elongated member 14 between collar 48 and the distal end of distal end cap 19. Spring member 41 forces the working head into an open position thus requiring the physician to push on the actuating mechanism to close the jaws. Thus, it is contemplated that the handle may be used to open or close by pushing or pulling the actuating mechanism and to provide a rotational motion to the working head by turning the actuating mechanism with keyed surfaces 47 and 48 removed from the inner workings of the handle.

It is to be understood that the above-described rotational surgical instrument is merely an illustrative embodiment of the principles of this invention and that other rotational instrument handles may be devised by those skilled in the art without departing from the spirit and scope of this invention. In particular, the invention has been described with the actuating mechanism being pulled or pushed, the keyed surfaces included to prevent rotation of the actuation link, and a variable tension spring member positioned between the actuating mechanism and the distal end cap to vary the actuating force of the handle. It is contemplated that any combination of these may be formed to provide a rotational surgical instrument. In particular, the keyed surfaces may be deleted to provide rotation of the working head if so equipped.

What is claimed is:

1. A rotational surgical instrument handle comprising:
   a cylindrical casing having a removable distal end cap, a removable proximal end cap, and a longitudinal passageway extending therebetween;
   an elongated member having a distal end, a proximal end positioned within said passageway of said casing, a proximal portion positioned through said removable distal end cap and longitudinally slidable between first and second positions with respect to said casing, and a longitudinal passageway extending between said distal and proximal ends thereof;
   an actuation link positioned and slidable within said longitudinal passageway of said elongated member and having a distal end and a proximal end extending beyond said proximal end of said elongated member and fixedly connected longitudinally to said removable proximal end cap; and
   an actuating mechanism positioned distally from said removable distal end cap of said casing and connected about said proximal portion of said elongated member for actuating said elongated member between said first and second positions.

2. The handle of claim 1 further comprising a first compression member positioned within said passageway of said casing, about said proximal end of said actuation link, and between said removable proximal end cap of said casing and said proximal end of elongated member.

3. The handle of claim 2 further comprising a second compression member positioned about said proximal portion of said elongated member between said actuating mechanism and said removable distal end cap of said casing.

4. The handle of claim 3 wherein said actuating mechanism is slidable between first and second positions from said removable distal end cap of said casing and wherein said actuating mechanism includes longitudinal adjustment means for varying a distance between said first and second positions.

5. The handle of claim 1 further comprising a first compression member positioned within said passageway of said casing, about said proximal end of said actuation link, about said proximal portion of said elongated member, and between said proximal end of said elongated member and said removable distal end cap of said casing.

6. The handle of claim 5 further comprising a second compression member positioned about said proximal portion of said elongated member between said actuating mechanism and said removable distal end cap of said casing.

7. The handle of claim 5 wherein said actuating mechanism is slidable between first and second positions from said removable distal end cap of said casing and wherein said actuating mechanism includes longitudinal adjustment means for varying a distance between said first and second positions.

8. The handle of claim 1 further comprising a first keyed surface fixedly positioned within said passageway of said casing and a second keyed surface fixedly positioned about said proximal portion of said elongated member and longitudinally engageable with said first keyed surface.

9. The handle of claim 1 wherein said removable distal end cap further includes a proximal end having said first keyed surface extending longitudinally therefrom.

10. The handle of claim 9 further comprising a second keyed surface fixedly positioned about said proximal end of said elongated member and longitudinally engageable with said first keyed surface.

11. The handle of claim 10 further comprising a compression member positioned within said passageway of said casing about said proximal end of said actuation link and between said second keyed surface and said distal end cap.

12. The handle of claim 11 further comprising a second compression member positioned around said proximal portion of said elongated member between said distal end cap and said actuating mechanism.

13. The handle of claim 12 wherein said actuating mechanism is slidable between first and second positions from said distal end cap and wherein said actuating mechanism includes longitudinal adjustment means for varying a distance between said first and second positions.

14. The handle of claim 11 further comprising a compression member positioned within said passageway of said casing, about said proximal portion of said elongated member and between said first and second keyed surfaces.

15. A rotational surgical instrument handle comprising:
- a cylindrical casing having a removable distal end cap, a removable proximal end cap, and a longitudinal passageway extending therebetween;
- an elongated member having a distal end, a proximal end positioned within said passageway of said casing, a proximal portion positioned through said removable distal end cap and longitudinally slidable between first and second positions with respect to said casing, and a longitudinal passageway extending between said distal and proximal ends thereof;
- an actuation link positioned and slidable within said longitudinal passageway of said elongated member and having a distal end and a proximal end extending beyond said proximal end of said elongated member and fixedly connected longitudinally to said removable proximal end cap;
- an actuating mechanism positioned distally from said removable distal end cap of said casing and connected about said proximal portion of said elongated member for actuating said elongated member between said first and second positions;
- a first keyed surface fixedly positioned about said removable distal end cap of said casing;
- a second keyed surface fixedly positioned about said distal end of said elongated member and longitudinally engageable with said first keyed surface; and
- a first compression member positioned in said passageway of said casing, about said of proximal end of said actuation link, and between said removable proximal end cap of said casing and said second keyed surface.

16. The handle of claim 15 further comprising a second compression member positioned about said proximal portion of said elongated member between said actuating mechanism and said removable distal end cap of said casing.

17. The handle of claim 15 further comprising pivotedly interconnected jaws connected to said distal end of said actuation link and said elongated member.

18. A rotational surgical instrument comprising:
- a cylindrical casing having a distal end, a proximal end, and a longitudinal passageway extending therebetween;
- a proximal end cap removably connected to said proximal end of said cylindrical casing;
- a distal end cap removably connected to said distal end of said cylindrical casing and having a longitudinal passageway extending therethrough;
- pivotedly interconnected first and second jaws having at least first and second positions;
- an elongated member having a distal end fixedly connected to said jaws, a proximal end positioned within said passageway of said casing, a proximal portion extending through said passageway of said distal end cap and slidable through said distal end cap, and a longitudinal passageway extending between said distal and proximal ends thereof;
- an actuation link positioned and slidable within said longitudinal passageway of said elongated member and having a distal end connected to said second jaw and a proximal end extending beyond said proximal end of said elongated member and fixedly connected longitudinally to said proximal end cap;
- a first keyed surface fixedly and laterally positioned about said distal end cap within said passageway of said casing;
- a second keyed surface fixedly and laterally positioned about said proximal end of said elongated member and longitudinally engageable with said first keyed surface;
- a first compression member positioned within said passageway of said casing about said of proximal end of said actuation link, and between said proximal end cap and said second keyed surface;
- an actuating mechanism positioned distally about said distal end cap and connected about said proximal portion of said elongated member for actuating said jaws between said first and second positions, said actuating mechanism being slidably between first and second positions from said proximal end cap and including longitudinal adjustment means for varying a distance between said first and second positions; and
- a second compression member positioned about said proximal portion of said elongated member and said distal end cap and said actuating mechanism, said longitudinal adjustment means also varying a compression force of said second compression member.

* * * * *